US00PP27487P2

(12) United States Plant Patent
van der Knaap

(10) Patent No.: US PP27,487 P2
(45) Date of Patent: Dec. 20, 2016

(54) ***SPATHIPHYLLUM* PLANT NAMED 'SPANOVA'**

(50) Latin Name: ***Spathiphyllum* Schott**
Varietal Denomination: Spanova

(71) Applicant: Leonardus Johannes Maria van der Knaap, Naaldwijk (NL)

(72) Inventor: Leonardus Johannes Maria van der Knaap, Naaldwijk (NL)

(73) Assignee: Nubilus B.V., Naalswijk (NL)

( * ) Notice: Subject to any disclaimer, the term of this patent is extended or adjusted under 35 U.S.C. 154(b) by 26 days.

(21) Appl. No.: 14/545,692

(22) Filed: Jun. 6, 2015

(51) Int. Cl.
*A01H 5/00* (2006.01)

(52) U.S. Cl.
USPC ..... Plt./364

(58) Field of Classification Search
USPC ..... Plt./364
See application file for complete search history.

*Primary Examiner* — Susan McCormick Ewoldt
(74) *Attorney, Agent, or Firm* — C. A. Whealy

(57) ABSTRACT

A new and distinct cultivar of *Spathiphyllum* plant named 'Spanova', characterized by its upright, outwardly arching and uniform plant habit; freely clumping growth habit; bushy and dense plants; glossy dark green-colored leaves; freely flowering habit; large white-colored spathes that are positioned above and between the foliar plane on strong and erect scapes; and good inflorescence longevity.

2 Drawing Sheets

Botanical designation: *Spathiphyllum* Schott.
Cultivar denomination: 'SPANOVA'.

BACKGROUND OF THE INVENTION

The present invention relates to a new and distinct cultivar of *Spathiphyllum* plant, botanically known as *Spathiphyllum* Schott. and hereinafter referred to by the cultivar name 'Spanova'.

The new *Spathiphyllum* plant is a product of a controlled breeding program conducted by the Inventor in Naaldwijk, The Netherlands. The objective of the breeding program is to create new year-round flowering *Spathiphyllum* plants that have glossy dark green-colored leaves, large white-colored spathes and good postproduction longevity.

The new *Spathiphyllum* plant originated from a cross-pollination made by the Inventor in March, 2011 of a proprietary selection of *Spathiphyllum* Schott. identified as code number 20121404-01, not patented, as the female, or seed, parent with a proprietary selection of *Spathiphyllum* Schott. identified as code number 20071881-28, not patented, as the male, or pollen, parent. The new *Spathiphyllum* plant was discovered and selected by the Inventor as a single plant within the progeny of the stated cross-pollination in a controlled greenhouse environment in Naaldwijk, The Netherlands in June, 2012.

Asexual reproduction of the new *Spathiphyllum* plant by tissue culture in a controlled environment in Naaldwijk, The Netherlands since July, 2012 has shown that the unique features of this new *Spathiphyllum* plant are stable and reproduced true to type in successive generations of asexual reproduction.

SUMMARY OF THE INVENTION

Plants of the new *Spathiphyllum* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Spanova'. These characteristics in combination distinguish 'Spanova' as a new and distinct *Spathiphyllum* plant:

1. Upright, outwardly arching and uniform plant habit.
2. Freely clumping growth habit; bushy and dense plants.
3. Glossy dark green-colored leaves.
4. Freely flowering habit.
5. Large white-colored spathes that are positioned above and between the foliar plane on strong and erect scapes.
6. Good inflorescence longevity.

Plants of the new *Spathiphyllum* differ from plants of the female parent selection in the following characteristics:

1. Leaves of plants of the new *Spathiphyllum* are broader than leaves of plants of the female parent selection.
2. Scapes of plants of the new *Spathiphyllum* are shorter than scapes of plants of the female parent selection.

Plants of the new *Spathiphyllum* differ from plants of the male parent selection in the following characteristics:

1. Leaves of plants of the new *Spathiphyllum* are darker green in color than leaves of plants of the male parent selection.
2. Scapes of plants of the new *Spathiphyllum* are shorter than scapes of plants of the male parent selection.

Plants of the new *Spathiphyllum* can also be compared to plants of *Spathiphyllum* Schott. 'Sparanke', disclosed in U.S. Plant Pat. No. 21,294. In side-by-side comparisons conducted in Naaldwijk, The Netherlands, plants of the new *Spathiphyllum* differed from plants of 'Sparanke' in the following characteristics:

1. Plants of the new *Spathiphyllum* were more freely clumping and bushier than plants of 'Sparanke'.
2. Leaves of plants of the new *Spathiphyllum* were broader than leaves of plants of 'Sparanke'.

3. Scapes of plants of the new *Spathiphyllum* were shorter than scapes of plants of 'Sparanke'.

BRIEF DESCRIPTION OF THE PHOTOGRAPHS

The accompanying photographs illustrate the overall appearance of the new *Spathiphyllum* plant showing the colors as true as it is reasonably possible to obtain in colored reproductions of this type. Colors in the photographs may differ slightly from the color values cited in the detailed botanical description which accurately describe the colors of the new *Spathiphyllum* plant.

The photograph on the first sheet is a side perspective view of a typical plant of 'Spanova' grown in a container.

The photograph on the second sheet is a close-up view of a typical inflorescence of 'Spanova'.

DETAILED BOTANICAL DESCRIPTION

The aforementioned photographs and following observations and measurements describe plants grown during the winter in 14-cm containers in a glass-covered greenhouse in Naaldwijk, The Netherlands. Plants were grown under conditions and cultural practices which approximate those generally used in commercial *Spathiphyllum* production. During the production of the plants, day temperatures ranged from 19° C. to 24° C., night temperatures ranged from 19° C. to 22° C. and light levels averaged 5 klux. Plants were 28 weeks old when the photographs and the detailed description were taken. In the following description, color references are made to The Royal Horticultural Society Colour Chart, 2007 Edition, except where general terms of ordinary dictionary significance are used.

Botanical classification: *Spathiphyllum* Schott. 'Spanova'.

Parentage:

*Female, or seed, parent*.—Proprietary selection of *Spathiphyllum* Schott. identified as code number 20121404-01, not patented.

*Male, or pollen, parent*.—Proprietary selection of *Spathiphyllum* Schott. identified as code number 20071881-28, not patented.

Propagation:

*Type*.—By tissue culture.

*Time to initiate roots, summer and winter*.—About eleven days at temperatures about 23° C.

*Time to produce a rooted young plant, summer*.—About 215 days at temperatures about 21° C.

*Time to produce a rooted young plant, winter*.—About 240 days at temperatures about 21° C.

*Root description*.—Medium in thickness, fibrous; white in color.

*Rooting habit*.—Moderately branching, medium density.

Plant description:

*Plant and growth habit*.—Upright and outwardly arching plant habit; overall plant shape, broadly inverted triangle; moderately vigorous growth habit.

*Clumping habit*.—Freely clumping habit, bushy and dense growth habit; about eight clumps develop per plant.

*Plant height, from soil level to top of leaf plane*.—About 36 cm.

*Plant height, from soil level to top of inflorescences*.—About 51.8 cm.

*Plant diameter or spread*.—About 56.8 cm.

*Leaf description*.—Arrangement: Alternate; simple. Length: About 25.3 cm. Width: About 8.3 cm. Shape: Narrowly ovate to ovate. Apex: Narrowly apiculate. Base: Attenuate. Margin: Entire; moderately undulate. Texture, upper and lower surfaces: Smooth, glabrous; slightly leathery. Luster, upper surface: Very glossy. Luster, lower surface: Glossy. Venation pattern: Pinnate. Color: Developing leaves, upper surface: Darker than between 141A and 143A. Developing leaves, lower surface: Close to between 138A and 147B. Fully expanded leaves, upper surface: Much darker and more intense than between N137A and N189A; venation, darker than 143A. Fully expanded leaves, lower surface: Close to N137C to N137D; venation, close to 143B to 143C. Petioles: Length (excluding geniculum): About 13.7 cm. Diameter, just below geniculum: About 3 mm. Diameter, at plant base: About 8 mm. Texture, upper and lower surfaces: Smooth, glabrous. Luster, upper and lower surfaces: Slightly glossy. Color, upper and lower surfaces: Close to 137A to 137B. Geniculum length: About 2.8 cm. Geniculum diameter: About 3.5 mm. Geniculum texture, upper and lower surfaces: Smooth, glabrous Geniculum luster, upper and lower surfaces: Slightly glossy. Geniculum color, upper and lower surfaces: Close to 143C. Wing length: About 12.2 cm. Wing diameter: About 6 mm. Wing color: Close to 143C.

Inflorescence description:

*Inflorescence arrangement and flowering habit*.—Moderately cupped erect spathes with columnar spadices held above and between the foliar plane on strong and erect scapes; flowering structures arise from leaf axils; plants begin flowering about five months after planting; freely and continuous flowering year-round under greenhouse conditions in The Netherlands; freely flowering habit, typically about nine inflorescences develop per plant.

*Fragrance*.—Faintly fragrant; fragrance, sweet and pleasant.

*Inflorescence longevity*.—Inflorescences last more than three weeks on the plant; inflorescences persistent.

*Spathe*.—Length: About 11.5 cm. Width: About 5.7 cm. Depth: About 3.4 cm. Shape: Ovate. Apex: Apiculate; twisting. Base: Obtuse. Margin: Entire; undulate. Texture, front and rear surfaces: Smooth, glabrous; slightly leathery. Luster, front surface: Slightly to moderately glossy. Luster, rear surface: Glossy. Color: When developing, front surface: Close to NN155A to NN155B; at the apex and main vein, close to 143A. When developing, rear surface: Close to between 155A and NN155A; at the apex and main vein, close to 143A. Fully developed, front surface: Close to NN155B; at the apex and main vein, close to 143A; with development, color becoming closer to between N144D and 145B. Fully developed, rear surface: Close to NN155A to NN155B; at the apex and main vein, close to 143A; with development, color becoming closer to between N144D and 145B.

*Spadix*.—Length: About 4 cm. Diameter: About 1.4 cm. Shape: Columnar, tapering towards the apex; apex, obtuse; base, obtuse; cross-section, rounded. Aspect: Close to erect, about 20° from scape axis. Color, immature: Slightly lighter than 160D. Color, mature: Close to 158D. Flowers: Quantity per spadix: Numerous, about 100. Shape: Rounded. Height: About 3 mm. Diameter: About 4 mm. Anther color: Close to 158A. Pollen amount: Moderate. Pollen color: Close to 155D. Stigma shape: Ovoid. Stigma color: Close to 158D. Ovary color: Close to 158D.

*Scapes*.—Length: About 37.5 cm. Diameter: About 4 mm. Strength: Strong. Aspect: Close to erect, about 5° from vertical. Color: Close to between 137A and 143A.

*Seeds and fruits*.—Seed and fruit development have not been observed on plants of the new *Spathiphyllum*.

Disease & pest resistance: Plants of the new *Spathiphyllum* have not been observed to be resistant to pathogens or pests common to *Spathiphyllum* plants.

Temperature tolerance: Plants of the new *Spathiphyllum* have been observed to be tolerant to high temperatures about 36° C. and to be hardy to USDA Hardiness Zone 11.

It is claimed:

1. A new and distinct *Spathiphyllum* plant named 'Spanova' as illustrated and described.

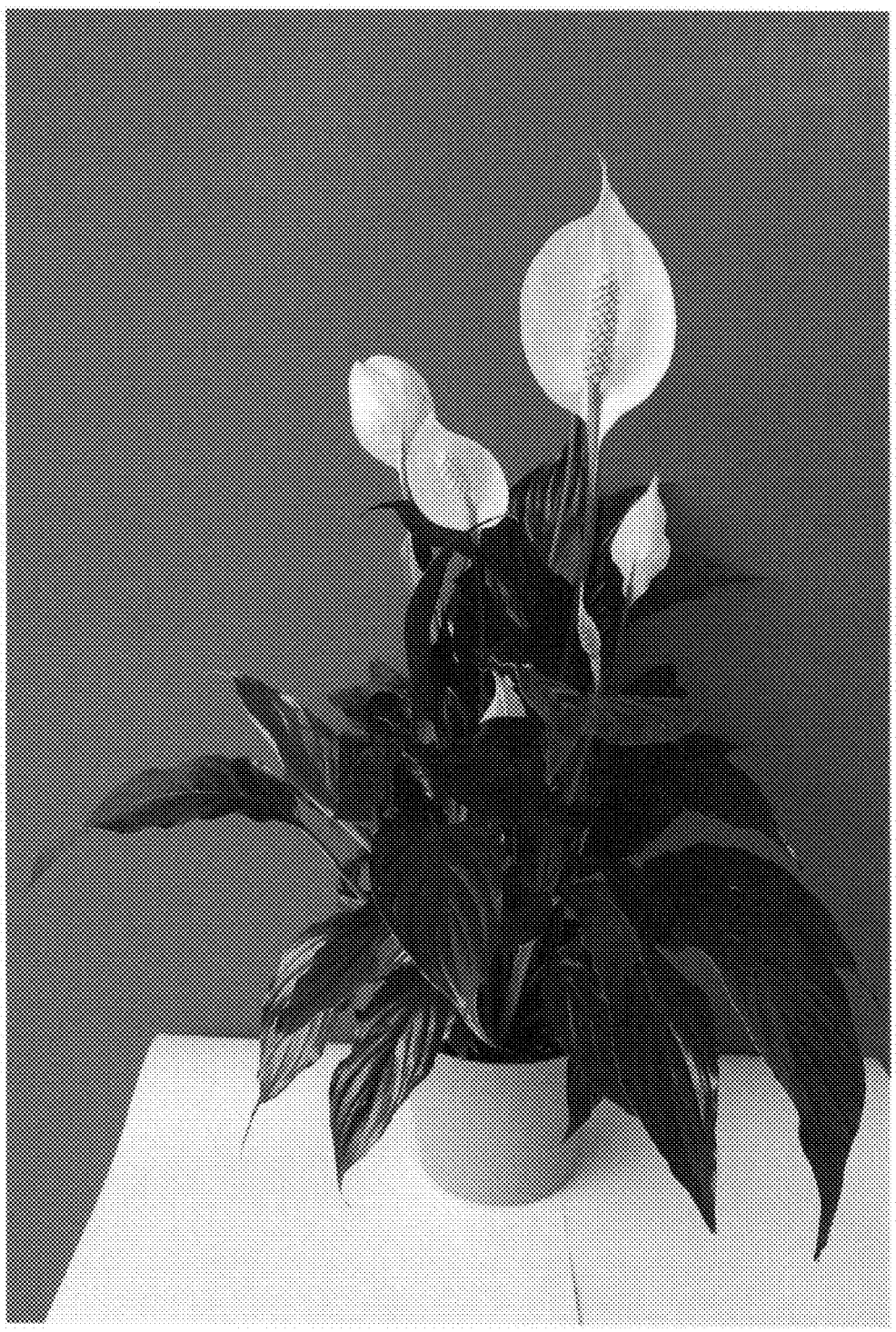

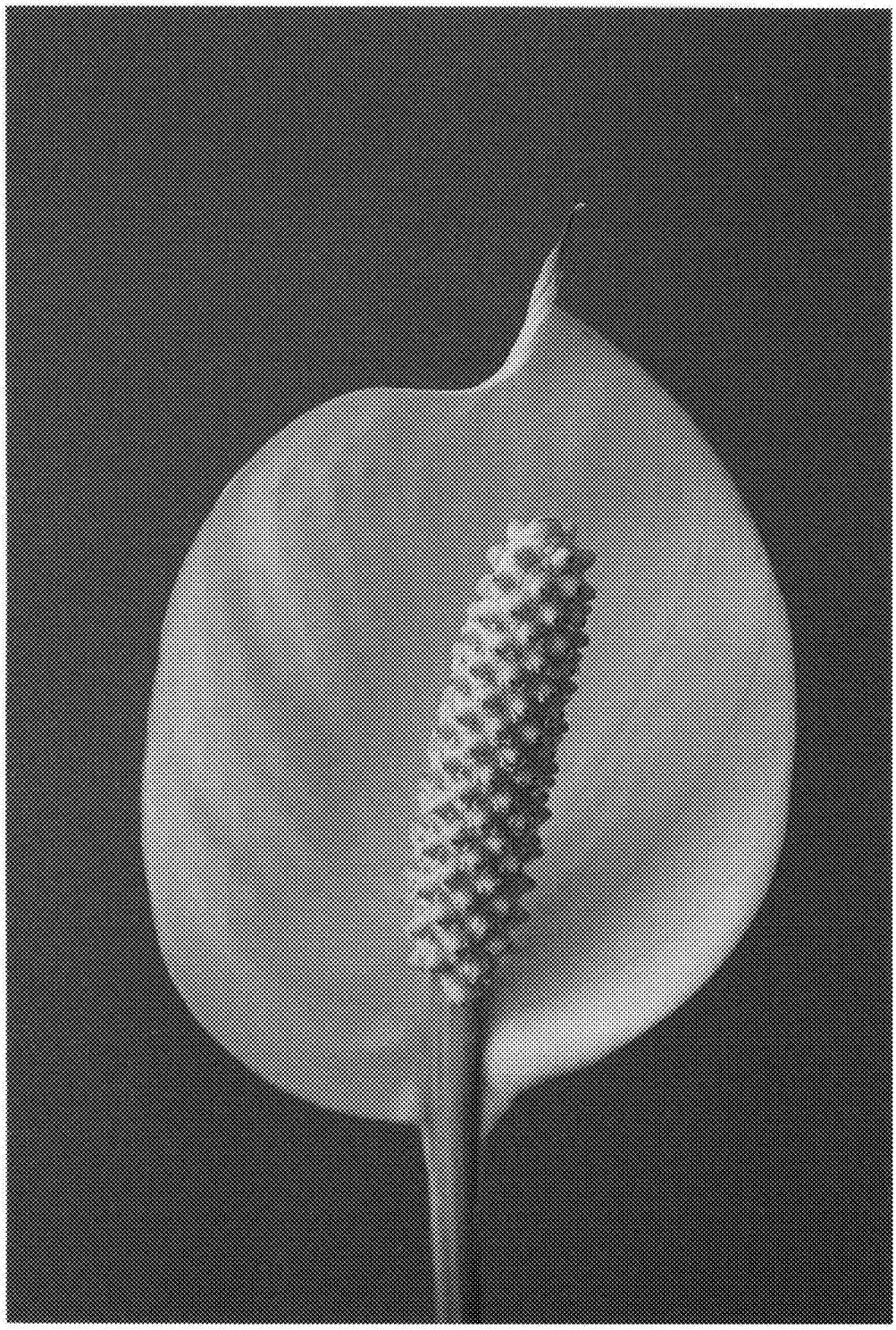

* * * * *